United States Patent [19]

Baasner et al.

[11] Patent Number: 4,518,812

[45] Date of Patent: May 21, 1985

[54] PROCESS FOR THE PREPARATION OF FLUORINATED NITROALKANES

[75] Inventors: Bernd Baasner; Hermann Hagemann, both of Leverkusen; Erich Klauke, Odenthal, all of Fed. Rep. of Germany

[73] Assignee: Bayer Aktiengesellschaft, Leverkusen, Fed. Rep. of Germany

[21] Appl. No.: 575,636

[22] Filed: Jan. 31, 1984

[30] Foreign Application Priority Data

Feb. 16, 1983 [DE] Fed. Rep. of Germany ....... 3305202

[51] Int. Cl.³ ...................... C07C 76/02; C07C 79/02
[52] U.S. Cl. .................................. 568/946; 568/924; 568/942
[58] Field of Search .................... 568/924, 942, 946

[56] References Cited

U.S. PATENT DOCUMENTS 2,864,853  12/1958  Bachman et al. .................. 260/467
3,118,004  1/1964   Hauptschein et al. ............. 260/644

FOREIGN PATENT DOCUMENTS 892442  4/1944  France .
14207   7/1964  Japan ................................. 568/946

OTHER PUBLICATIONS

Pierce et al., Quantitative Analysis, 3rd Ed., 1948, John Wiley & Sons, Inc., N.Y., pp. 428 to 429.
Talybov et al., Chem. Abs., vol. 97, 5760K, (1982), published Jul. 5, 1982.

*Primary Examiner*—Leland A. Sebastian

*Attorney, Agent, or Firm*—Sprung, Horn, Kramer & Woods

[57] ABSTRACT

In the conjugated nitrofluorination of an olefin by reacting an olefin of the formula

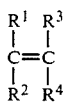

in which $R^1$, $R^2$, $R^3$ and $R^4$ each independently is hydrogen, fluorine, chlorine, bromine, alkyl, halogenoalkyl or cycloalkyl, or $R^2$ and $R^4$ together are an alkylene radical of 3 to 6 carbon atoms, with hydrogen fluoride and nitric acid to produce an α-fluorinated nitroalkane of the formula

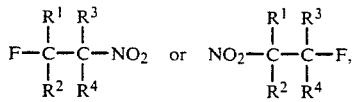

the improvement which comprises effecting the reaction in a vessel protected against corrosion employing about 1 to 1.1 mols of hydrogen fluoride and about 1 to 2 mols of nitric acid per mol of olefin. The process uses much less HF than heretofore and the products are useful intermediates in making herbicides. Some of the products are new.

11 Claims, No Drawings

PROCESS FOR THE PREPARATION OF FLUORINATED NITROALKANES

The invention relates to an improved process for the preparation of α-fluorinated nitroalkanes and -cycloalkanes by conjugated nitrofluorination of the corresponding olefines. Some of the α-fluorinated nitroalkanes which can be prepared according to the invention are already known and can be used as intermediates for the preparation of certain herbicides.

Fluorinated nitroalkanes can be prepared by various processes, for example by reaction of aliphatic carboxylic acids, which contain nitro groups, with $SF_4/BF_3$ (compare Tetrahedron 26, page 5737 (1970)). The necessary starting materials must first be prepared, and the subsequent fluorination process is extremely elaborate and is completely unsuitable for industrial use.

Moreover, it has been disclosed in reports by Russian authors that aliphatic α-fluorinated nitro compounds can be prepared by the reaction of olefins in anhydrous hydrogen fluoride with concentrated nitric acid in accordance with the general equation below:

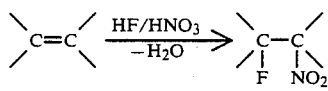

(compare Dokl.Akad.Nauk.SSSR 149, pages 222-5 (1963) (Engl.) and Izvest. Akad.Nauk.SSSR 1963, pages 1794-7 (Engl.)).

This reaction is denoted conjugated nitrofluorination and, in principle, appears attractive for industrial use. However, it emerges that the laboratory procedures known from the Russian publications mentioned are likewise completely unsuitable for direct transfer to large industrial scale.

In the previously known procedure, the hydrogen fluoride acts both as a fluorinating agent and as a solvent and it is employed in very large excess. Since an equimolar amount of water is produced in the reaction, an aqueous mixture of HF and $HNO_3$ results during the reaction, and this is highly corrosive for the steel stirring vessels which are customarily used. In order to limit this corrosion it is necessary to use a large excess of HF; by this means, the injurious concentration of water can be decreased to such an extent that it is even possible to reach the range of resistance of the materials of the relevant reaction vessels. In the known process, it is necessary to employ 5 to 100 mols of hydrogen fluoride to 1 mol of olefin, in other words at least a 500 mol-% excess. The further processing of the resulting aqueous acid mixture is very cost-intensive and industrially difficult. Recovery of the excess hydrofluoric acid in the anhydrous form, as is necessary for renewed reaction, from the resulting aqueous solution is virtually impossible with reasonable industrial expenditure.

It has now been found, surprisingly, that conjugated nitrofluorination can be carried out with a considerably lower molar excess of hydrogen fluoride, mainly with a maximum of 10% excess, relative to olefin employed, without losses in yield occurring. At the same time, 1 to 2 mols of nitric acid are employed for 1 mol of olefin. Moreover, it has been found that this reaction can also be carried out with equal success when aqueous hydrofluoric acid is employed in place of anhydrous hydrogen fluoride; an excess of 10 mol-% of hydrogen fluoride relative to the olefin even suffices for this new variant of the process. Both of the new variants of the process are carried out in equipment protected against corrosion by aqueous hydrofluoric acid.

Thus the invention relates to a process for the preparation of α-fluorinated nitroalkanes of the general formula

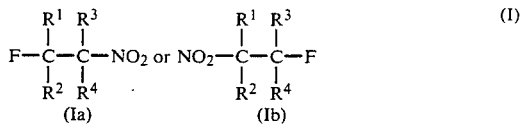

in which, $R^1$, $R^2$, $R^3$ and $R^4$ are identical or different and individually represent hydrogen, fluorine, chlorine, bromine, alkyl, halogenoalkyl or cycloalkyl, or $R^1$ and $R^3$ have the meaning indicated and $R^2$ and $R^4$ together represent an alkylene group having 3-6 carbon atoms, by conjugated nitrofluorination of the corresponding olefins characterized in that 1 to a maximum of 1.1 mols of hydrogen fluoride and 1 to 2 mols of nitric acid are employed per mol of olefin of the formula

in which $R^1$, $R^2$, $R^3$ and $R^4$ have the meaning indicated above, the reaction being carried out in equipment protected against corrosion and it also being possible for the hydrogen fluoride to be employed in the form of an aqueous solution.

It is possible to deduce, using the known Markownikoff rule, whether the products formed have the formula (Ia) or (Ib) or, in exceptional cases, are mixtures of (Ia) and (Ib).

Considerable amounts of hydrogen fluoride can be saved by the possibility which has been discovered of it being possible to carry out the conjugated nitrofluorination with a considerably lower excess of HF (that is to say a maximum of 10 mol-% compared with 500 to 10,000 mol-% in the previously known procedure) while achieving equally good yields of α-fluoronitroalkanes. Thus the reaction can be carried out at much more reasonable cost and more reliably, and it is now also suitable for use on a large industrial scale.

The olefins to be employed as the starting materials are generally defined by formula (II). In this formula, $R^1$, $R^2$, $R^3$ and $R^4$, which can be identical or different, preferably represent hydrogen, fluorine, chlorine, bromine, alkyl having 1-4 carbon atoms, halogenoalkyl having 1-4 carbon atoms (and preferably with fluorine and chlorine as the halogen atom) or cycloalkyl having 3-8 carbon atoms, or $R^1$ and $R^3$ represent the radicals indicated above, and $R^2$ and $R^4$ together represent an alkylene group having 3-4 carbon atoms.

Olefins which can be used according to the invention are already known and can be prepared by generally known methods. For example, the olefins mentioned below can be employed as starting materials: chloroethene, 1,1-dichloroethene, 1,1-difluoroethene, fluoroethene, tetrafluoroethene, trifluorochloroethene, 1,2- dichloro-1,2-difluoroethene, trifluoroethene, 1-chloro-1,2-difluoroethene, 1,1-dichloro-2-fluoroethene, ethene, 1-chloro-1-fluoroethene, 1,1-dichloro-2,2-difluoroethene, trichloroethene, 1,2-dichloro-1-fluoroethene, propene, 1,1-difluoropropene, 1,1-dichloropropene, 1-chloro-1-fluoropropene, 2-fluoropropene, 2-chloropropene, 1,1-dichloro-3,3-dimethyl-1-propene, hexafluoropropene, 1,1,3,3,3-pentafluoropropene, 1,1-dichloro-2,3,3,3-tetrafluoropropene, 1,1,2-trichloro-3,3-trifluoropropene, 1,1,2,3-tetrachloro-3,3-difluoropropene, 3-chloropropene, 2,3-dichloropropene, 3,3,3-trifluoropropene, bromoethene, 1,1-difluorobutene, 1-chloro-1-fluorobutene, 1,1-dichlorobutene, cyclohexene and 2-(fluoromethyl)-3-fluoro-1-propene.

The process according to the invention is carried out in equipment protected against corrosion, which consists, for example, of Teflon perfluoro-polyethylene, polyethylene or other materials inert to aqueous hydrofluoric acid, or in steel stirring vessels which are lined with these materials, in which it is possible to operate under normal pressure or under elevated pressure. In principle, the sequence in which the reaction components are mixed together in this process is arbitrary.

However, it is particularly advantageous for carrying out the process first to introduce a mixture of aqueous hydrofluoric acid and nitric acid into a stirring vessel or stirring autoclave which is resistant to corrosion by aqueous hydrofluoric acid, and then to add the olefine.

It is true that the excess of hydrogen fluoride compared with the olefin employed can be arbitrarily large but, in the sense of the invention, a molar ratio of 1 to 1.1 mols of hydrogen fluoride per mol of olefin (II) is completely adequate.

In addition, 1 to 2 mols of nitric acid are employed per 1 mol of olefin (II). A ratio of 1 to 1.2 mols of nitric acid per mol of olefin is preferred, and 1 mol of nitric acid per mol of olefin is particularly preferred.

The concentration of the mixture of acids in water can be 10 to 95%, preferably 40 to 80%, and very particularly preferably 50 to 70%. It is true that the reaction also takes place at high dilution, but the reaction time becomes disproportionately long by reason of the poor solubility of the olefins to be reacted in the mixture of acids.

After first introducing the mixture of acids, the olefin to be reacted is introduced into the reaction vessel at temperatures from −80° to +120° C., preferably from −60° to +80° C., by being passed in, condensed in, added dropwise or injected into the closed reaction vessel. The actual reaction temperatures are likewise between −80° and +120° C., preferably between −20° and +80° C. The reaction takes place under normal pressure or the inherent pressure which builds up in the closed reaction vessel during the course of the reaction. However, it is also possible to operate under elevated pressure, for example up to 50 bar, this pressure being reached by injecting an inert gas, such as nitrogen. The reaction time is 0.5 to 48 hours, a reaction time of 2 to 16 hours generally sufficing.

The working up and isolation of the reaction products are carried out by customary methods.

The α-fluoro nitroalkanes (I) which can be prepared according to the invention can be used, for example, as intermediates for the preparation of fluorine-containing herbicidal active compounds, for example of the class of sym-triazines. It is possible smoothly to reduce the nitro group in the compounds (I) to the amino group by catalytic hydrogenation, the corresponding α-fluorinated alkylamines or cycloalkylamines thus being obtained in high yields. The latter can be reacted in a known manner with cyanuric chloride or cyanuric fluoride to give known sym-triazines which are substituted by the corresponding fluoroalkylamino groups and are known to have potent herbicidal properties (compare, for example, DE-OS (German Published Specification) No. 3,127,861, DE-OS (German Published Specification) No. 3,218,201 and DE-OS (German Published Specification) No. 3,218,966).

Thus, for example, starting from 1-methyl-2,2,2-trifluoronitroethane, the herbicidally active compound 2-chloro-4-ethylamino-6-(1-methyl-2,2,2-trifluoroethylamino)-s-triazine is obtained by the following routes:

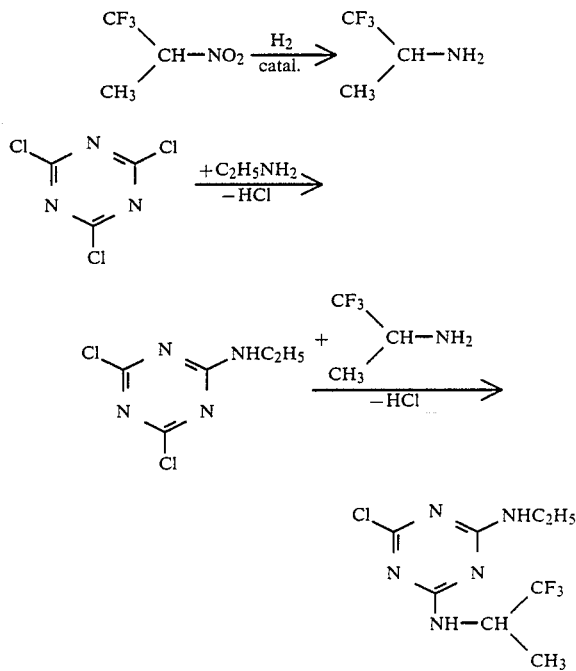

The Examples which follow serve further to illustrate the invention.

EXAMPLES

Example 1

(a) according to the invention:

220 g (11 mols) of hydrogen fluoride, 780 g (43.3 mols) of water and 630 g (10 mols) of nitric acid (d=1.51) were introduced first into a stirring vessel lined with polyethylene and, while cooling at 0° to +10° C., 640 g (10 mols) of 1,1-difluoroethene were passed in. The reaction mixture was allowed to warm to room temperature and then stirred for 8 hours. The reaction mixture was then diluted with 1 liter of water, the organic phase was separated off and the aqueous phase was extracted three times with 200 ml of dichloromethane each time. The combined organic phases were washed with sodium bicarbonate solution and with water to neutrality, and dried over magnesium sulphate. After distilling out the solvent, 850 g (=66% of theory) of 2,2,2-trifluoronitroethane of boiling point 91°–92° C. were obtained; $n_D^{20}$: 1.3290.

(b) Comparison experiment (according to Izvest. Akad. Nauk. SSSR 1963, pages 1794–7 (Engl.)):

1,400 g (70 mols) of hydrogen fluoride (anhydrous) and 630 g (10 mols) of nitric acid (d=1.51) were introduced first into a stirring steel autoclave and, while cooling at −30° to −10° C. in ice/salt, 640 g (10 mols) of 1,1-difluoroethene were passed in. The reaction mixture was allowed to come to room temperature in about 4 hours and then poured onto 1.5 kg of ice, and the organic phase was separated off and the aqueous phase was extracted three times with 200 ml of dichloromethane each time. The combined organic phases were washed with sodium bicarbonate solution and with water to neutrality, and then dried over magnesium sulphate. After distilling out the solvent, 790 g (=61% of theory) of 2,2,2-trifluoronitroethane of boiling point 91°–92° C. were obtained; $n_D^{20}$: 1.3285.

The compounds listed in Table 1 below were prepared in analogy to Example 1(a):

TABLE 1

| Example No. | Olefine (II) | Products (I) | Boiling Point [°C.] | $n_D^{20}$ | Yield (%) |
|---|---|---|---|---|---|
| 2 | $CHCl=CH_2$ | $CFClH-CH_2-NO_2$ | 55-7/40 mbar | 1.4235 | 65 |
| 3 | $CHF=CH_2$ | $CF_2H-CH_2-NO_2$ | 25/20 mbar | 1.3648 | 69 |
| 4 | $CCl_2=CH_2$ | $CFCl_2-CH_2-NO_2$ | 57/30 mbar | 1.4370 | 82 |
| 5 | $CBrH=CH_2$ | $CFBrH-CH_2-NO_2$ | 65-6/30 mbar | 1.4658 | 56 |
| 6 | $CCl_2=CH-CH_3$ | $CFCl_2-CH(NO_2)-CH_3$ | 55/20 mbar | 1.4390 | 69 |
| 7 | $CFCl=CH-CH_3$ | $CF_2Cl-CH(NO_2)-CH_3$ | 34-5/20 mbar | 1.3870 | 75 |
| 8 | $CF_2=CH-CH_3$ | $CF_3-CH(NO_2)-CH_3$ | 99-100/1 bar | 1.3386 | 82 |
| 9 | $CH_3-CF=CH_2$ | $CH_3-CF_2-CH_2-NO_2$ | 40-2/25 mbar | 1.3704 | 76 |
| 10 | $CFCl=CH_2$ | $CF_2Cl-CH_2-NO_2$ | 55-6/30 mbar | 1.3828 | 74 |

The α-fluoronitroalkanes of Examples 3, 5, 6, 7, 9 and 10 are new compounds and the invention likewise relates to them. The α-fluoronitroalkanes of Examples 1 to 10 can be hydrogenated to the corresponding amines, which can then be reacted with chlorotriazines as described hereinabove to prepare herbicidally active compounds.

It will be appreciated that the instant specification and examples are set forth by way of illustration and not limitation, and that various modifications and changes may be made without departing from the spirit and scope of the present invention.

We claim:

1. In the conjugated nitrofluorination of an olefin by reacting an olefin of the formula $$\begin{array}{c} R^1 \quad R^3 \\ | \quad\; | \\ C=C \\ | \quad\; | \\ R^2 \quad R^4 \end{array}$$

in which

R[1], R[2], R[3] and R[4] each independently is hydrogen, fluorine, chlorine, bromine, alkyl, halogenoalkyl or cycloalkyl, or R[2] and R[4] together are an alkylene radical of 3 to 6 carbon atoms, with hydrogen fluoride and nitric acid to produce an α-fluorinated nitroalkane of the formula

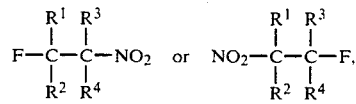

the improvement which comprises effecting the reaction in a vessel protected against corrosion employing about 1 to 1.1 mols of hydrogen fluoride and about 1 to 2 mols of nitric acid per mol of olefin.

2. A process according to claim 1, wherein the hydrogen fluoride is employed in the form of an aqueous solution.

3. A process according to claim 1, wherein the reaction is carried out at a temperature between about −80° and +120° C.

4. A process according to claim 1, wherein the reaction is carried out at a temperature between about −20° and +80° C.

5. A process according to claim 1, wherein the reaction is carried out at a pressure of about 1–50 bar.

6. A process according to claim 1, wherein about 1–1.2 mols of nitric acid are employed per mol of olefin.

7. A process according to claim 1, in which the olefin is $$CF_2=CH-CH_3$$

and the α-fluorinated nitroalkane is $$CF_3-CH(NO_2)-CH_3$$

8. The process according to claim 7, wherein the hydrogen fluoride is employed in the form of an aqueous solution, about 1–1.2 mols of nitric acid are employed per mol of olefin and the reaction is carried out at a temperature between about −20° and +80° C. and a pressure of about 1 to 50 bar.

9. A process according to claim 1, in which the olefin is selected from the group consisting of
1,1-difluoroethene,
chloroethene,
fluoroethene, 1,1-dichloroethene,
bromoethene,
2-fluoropropene
1-chloro-1-fluoro-ethene.

10. A process according to claim 1, wherein the vessel surface which contacts the reactants is perfluoropolyethylene.

11. An α-fluoronitroalkane selected from the group consisting of
2,2-difluoronitroethane,
2,2-dichloro-2-fluoro-1-methylnitroethane,
2-chloro-2,2-difluoro-1-methylnitroethane,
2,2-difluoronitropropane and
2-chloro-2,2-difluoronitroethane.

* * * * *

UNITED STATES PATENT AND TRADEMARK OFFICE
CERTIFICATE OF CORRECTION

PATENT NO. : 4,518,812
DATED : May 21, 1985
INVENTOR(S) : Bernd Baasner, et al

It is certified that error appears in the above-identified patent and that said Letters Patent is hereby corrected as shown below:

Col. 4, line 66        Before "66%" delete "=" and substitute -- $\triangleq$ --

Col. 5, line 15        Before "61%" delete "=" and substitute -- $\triangleq$ --

Col. 6, line 58        Delete "The" and substitute --A--

Signed and Sealed this

Fifteenth Day of October 1985

[SEAL]

Attest:

DONALD J. QUIGG

*Attesting Officer*      *Commissioner of Patents and Trademarks—Designate*